United States Patent [19]

Salzman et al.

[11] 3,946,239

[45] Mar. 23, 1976

[54] ELLIPSOIDAL CELL FLOW SYSTEM

[75] Inventors: Gary C. Salzman; Paul F. Mullaney, both of Los Alamos, N. Mex.

[73] Assignee: The United States of America as represented by the United Energy Research and Development Administration, Washington, D.C.

[22] Filed: Jan. 24, 1975

[21] Appl. No.: 544,026

[52] U.S. Cl. .............................. 250/461 B; 356/39
[51] Int. Cl.² ......................................... G01N 21/38
[58] Field of Search ...... 250/461 B; 209/3, 4, 111.5; 356/39, 97, 98

[56] References Cited
UNITED STATES PATENTS 3,864,571  2/1975  Stillman et al. ................. 250/461 B

*Primary Examiner*—Davis L. Willis
*Attorney, Agent, or Firm*—Dean E. Carlson; Robert W. Weig

[57] ABSTRACT

The disclosure relates to a system incorporating an ellipsoidal flow chamber having light reflective walls for low level light detection in practicing cellular analysis. The system increases signal-to-noise ratio by a factor of ten over prior art systems. In operation, laser light passes through the primary focus of the ellipsoid. A controlled flow of cells simultaneously passes through this focus so that the laser light impinges on the cells and is modulated by the cells. The reflective walls of the ellipsoid reflect the cell-modulated light to the secondary focus of the ellipsoid. A tapered light guide at the secondary focus picks up a substantial portion of modulated reflective light and directs it onto a light detector to produce a signal. The signal is processed to obtain the intensity distribution of the modulated light and hence sought after characteristics of the cells. In addition, cells may be dyed so as to fluoresce in response to the laser light and their fluorescence may be processed as cell-modulated light above described. A light discriminating filter would be used to distinguish reflected modulated laser light from reflected fluorescent light.

4 Claims, 3 Drawing Figures

U.S. Patent   March 23, 1976   3,946,239
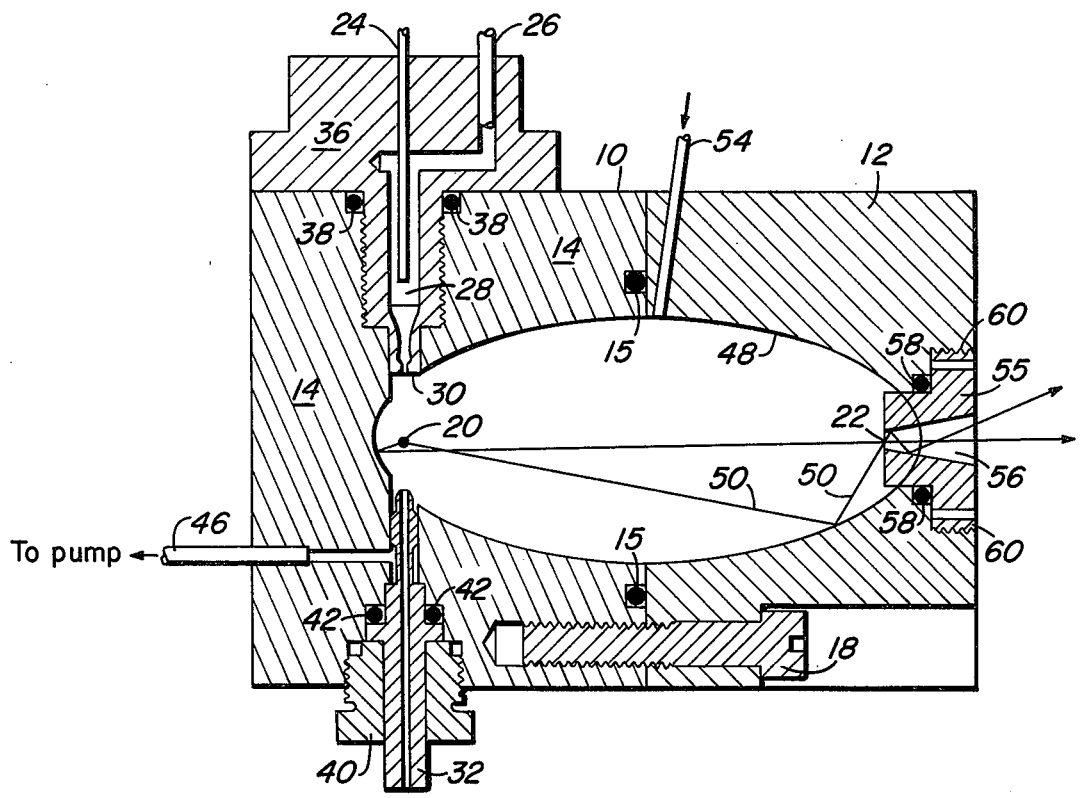
Fig. 1
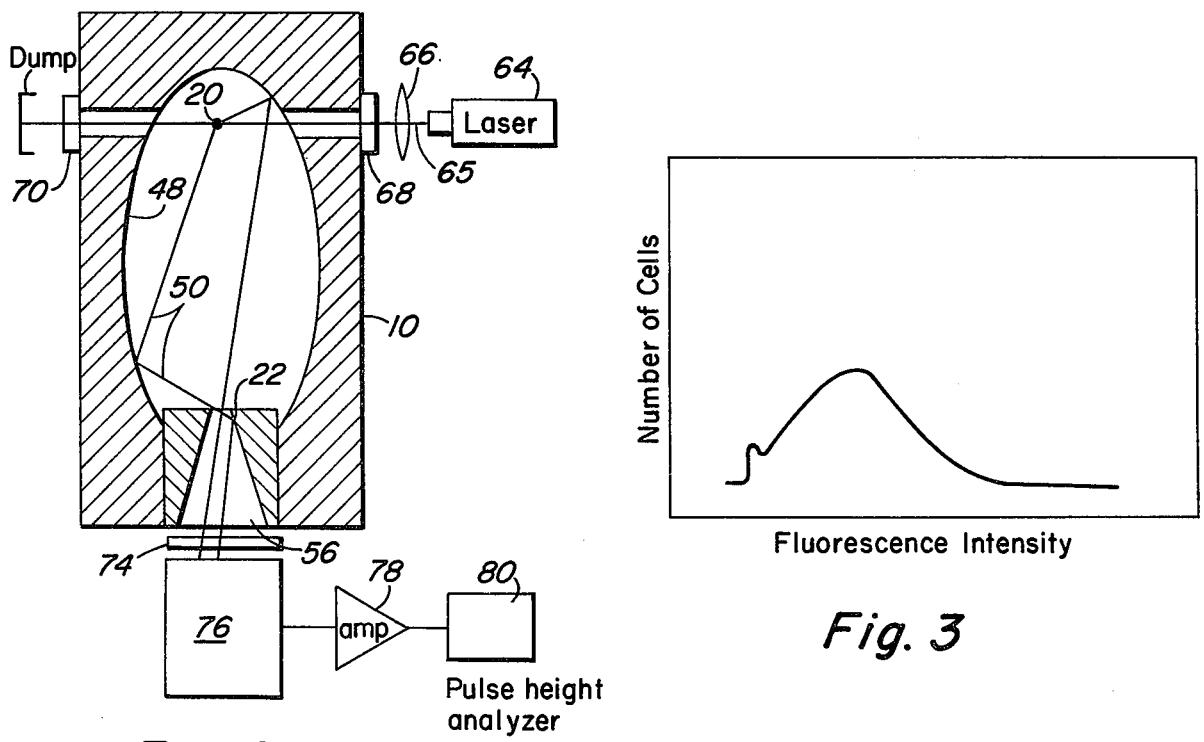
Fig. 2
Fig. 3

ELLIPSOIDAL CELL FLOW SYSTEM

The invention described herein was made in the course of, or under, a contract with the U.S. Atomic Energy Commission.

FIELD OF THE INVENTION

The invention relates to cellular analysis and more particularly to cellular analysis utilizing light modulation and fluorescence by cells to determine certain characteristics thereof.

BACKGROUND OF THE INVENTION

In cytology, there is an ever-increasing demand for automatic cellular counting, volumetric differentiation and analysis. At the present time a two level screening process manually accomplishes screening of cytological material such as for the detection of cancerous or malignant cells, and for sizing and counting the cells present in a particular amount of material. An observer capable of determining which samples apparently contain abnormal cells and of determining the size cell one hopes to count within a sample first visually prescreens the cells. A trained cytotechnologist or pathologist who makes a final determination as to whether the cells of these samples are inded cancerous then examines the abnormal cell-containing samples. This method fairly accurately finds cancerous cells, but has a number of disadvantages. First, it is slow, requiring considerable technician time. Second, it is costly due to the human time involved. Third, it is nonquantitative in that the criterion of abnormality as well as the amount of cells present in a particular volumetric sample are primarily subjective. Because of the time and costs involved, it is generally not practicable to examine large populations of individuals using these prior art techniques.

It is therefore desirable to have a system for automatically determining the volumetric distribution of a sample of cells, to normalize light signals from a cell analyzer such as that disclosed in U.S. Pat. No. 3,824,402 to Mullaney et al., assigned to the U.S.A. as represented by the U.S.A.E.C.

Presently, prior art electrical analysis devices utilize a simple orifice with two electrodes at either end of the orifice disposed in a surrounding saline solution. An individual cell moving through the orifice displaces some of the conductive fluid in the orifice. Because the conductivity of the cell is less than that of the fluid it displaces, the resistance of the orifice contents increase due to the presence of the cell by an amount related to the volume of the cell. Electrical circuits connected to the electrodes sense this change of resistance and produce a signal pulse. In such a device, the desired signal from the cell mixes with undesired noise signals which originate outside of the orifice, because the sensing electrodes are disposed outside of the orifice, to produce a low signal-to-noise ratio.

Prior art flow systems such as those disclosed in U.S. Pat. No. 3,710,933 to Fulwyler et al., assigned to the U.S.A. as represented by the U.S.A.E.C., U.S. Pat. No. 3,560,754 to Kamentsky, and U.S. Pat. No. 3,675,768 to Sanchez have been applied to these problems in order to provide automatic methods of discriminating and classifying normal and abnormal cells. Flow system analysis, as applied by these prior art systems, allows observation of individual cells as they flow in suspension sequentially through a small detection volume. Large numbers of cells are observed in a short period of time and rapid automatic prescreening procedures are applied. Parameters used in evaluation of the cells are light absorption by the cells, fluorescence emitted by stained cells in response to light incident thereon, cell produced scattering of the light incident on the cells, and the volume of the particles observed.

One of the problems of the prior art systems is that fluorescence detectors currently used with the flow microfluorometers such as disclosed in U.S. Pat. No. 3,824,402 to Mullaney et al., and U.S. Pat. No. 3,710,933 to Fulwyler et al. collect only about 3% of the available fluoresced light.

In accordance with the invention, the ellipsoidal cavity flow cell thereof collects approximately 75% of the available fluorescent light. This provides a signal increase of at least 20 times and an increase in signal-to-noise ratio of at least 10 times over the Mullaney and Fulwyer et al. devices. In practice a signal-to-noise ratio increase of 15 times over the above mentioned systems has been obtained. Thus the system of the invention is highly useful in investigating very weakly fluorescing dyes bound to cells, the fluorescence of very small particles, as well as very small cells and other cells which weakly modulate laser light.

SUMMARY OF THE INVENTION

In accordance with the invention, there is provided a cell flow and fluorescence detector comprising an essentially ellipsoidal flow chamber having primary and secondary foci and having walls at least somewhat reflective in a selected portion of the spectrum, a device for passing cells through the primary focus, a light source directed on the primary focus for illuminating the cells as they pass through the primary focus so that the light scattered by the cells impinges on and reflects from the walls of the ellipsoidal flow chamber, and a detector for detecting the cell-modulated light as reflected from the primary focus, preferably onto the secondary focus. Alternatively, where cells are stained so as to fluoresce when light from the illuminating source impinges thereon, a detector is provided for receiving the fluoresced light as reflected onto the secondary foci. Light discriminating filters can be introduced between the detector and the secondary focus so that only a selective wavelength or wavelengths arrive at the detector. The detector converts the light signal into an electrical signal which is processed to provide a light intensity distribution indicative of cell characteristics and the distribution of cells as they pass through the primary focus ellipsoidal flow chamber.

BRIEF DESCRIPTION OF THE DRAWINGS

Other objects and advantages of the present invention will be apparent to those skilled in the art from the following description with reference to the appended claims wherein like numbers denote like parts and wherein:

FIG. 1 shows a cross section of an ellipsoidal flow chamber in accordance with the invention;

FIG. 2 schematically illustrates a preferred embodiment of the system of the invention; and FIG. 3 shows an exemplary graphical representation of an output of the system of FIG. 2.

DETAILED DESCRIPTION OF THE INVENTION

Reference is now made to FIG. 1 which shows a cross sectional view of the ellipsoidal flow chamber of the invention. As can be seen, an essentially ellipsoidal flow chamber comprising a housing 10 is formed by fastening together a first block 12 and a second block 14. These blocks can be fastened together in a conventional manner such as with a machine screw 18. O-ring 15 provides a seal between blocks 12 and 14. The locations of a primary focus 20 and a secondary focus 22 within the ellipsoidal cavity are indicated. Cells pass through a sample inlet tube 24 and mix with a sheathing fluid passed through a sheath inlet tube 26 in an area 28 of a nozzle 30. The sheathed cells then pass through nozzle 30 so that they flow through primary focus 20. After the liquid sheathed cells go through focus 20 they outlet through an outlet device 32. The sample inlet tube and sheath inlet tube are set within a screw-in plug 36 which is sealed to block 14 by an O-ring 38 so as to form an airtight seal. Outlet 32 is set in another plug 40 which is screwed in and sealed against block 14 by an O-ring 42. The ellipsoidal flow chamber is preferably filled with water or another desirable liquid medium through conduit 54 in block 12. The medium passes out of the cavity through conduit or tube 46.

Light such as from a laser beam passes through primary focus 20 in a direction perpendicular to the plane of the paper containing the drawing. The detail of how it passes through this locus is shown in FIG. 2 and will be more particularly described hereinafter.

In the preferred embodiment of the invention, the ellipsoidal cavity contained within blocks 12 and 14 is coated with a highly reflective layer of gold 48. What other reflective coatings may be used will be obvious to those skilled in the art. Which particular reflecting coating one uses is determined by the wavelength or wavelengths of light desired to be reflected in practicing the invention in any given application.

It is well known to those skilled in the art that light passing through an ellipsoid focus, other than that directly passing through one focus to another, will be reflected off the walls of the ellipsoid and through its other focus. Therefore as can be seen in FIG. 1, an exemplarly beam 50 from focus 20 reflects off the wall of the ellipsoid and arrives at secondary focus 22. The terms primary and secondary focus have been selected purely as a matter of convenience and to better explain the invention. In accordance with the invention, the primary focus is the focus through which the cells and the laser beam mutually pass and the secondary focus is the point where the reflected beams collect. A collection plug 55 comprises a truncated cone light conducting medium 56 such as a transparent medium of plastic, quartz or glass. Light conducting medium 56 and its geometry is shown in the preferred embodiment as a truncated cone, but may be in any shape or formed from any material that will do the job. Plug 55 preferably seals to block 12 with O-rings 58 and may be screwed into block 12 on threads 60 so as to form a tight seal therewith.

In the preferred embodiment of the invention the ellipsoidal cavity need only be water tight. It will be obvious to those skilled in the art that the tightness must be such as to sufficiently contain whatever liquid or gas the practicer of the invention desires to utilize within the cavity.

So as to be able to continually or periodically circulate fresh water or whatever medium fills the cavity, tube 54 continually or periodically introduces fresh portions of the medium into the interior of the cavity and tube 46 extracts old portions therefrom. The sites for the introduction and the extraction of liquid from the cavity is purely a matter of experiment and other sites may prove desirable to those practicing the invention. The introduction and extraction of fluid medium keeps the medium fresh, and clear of debris from the stream of cells.

In operation, as can best be seen in FIG. 1, cells, after passing though sample inlet 24 are sheathed by a fluid medium, which preferably is the same fluid that fills the cavity. Cells and sheathing liquid combine in the area 28 of nozzle 30, so that the liquid sheathed cells pass through the primary focus 20 and outlet through tube 32. All the while fresh liquid may be introduced through tube 54 and extracted through tube 46.

FIG. 2 shows the ellipsoidal cavity housing 10 in use in a preferred system in accordance with the invention. For the sake of clarity and because they have already been shown in FIG. 1, the cell introduction and outlet structures and the conduits 54 and 46 for introducing and extracting liquid medium from the interior of the ellipsoid are not shown in FIG. 2. A source of light such as a laser 64 passes a beam 65 through a columination device such as a lens 66 and through the primary focus 20 within the ellipsoidal cavity in housing 10. Windows 68 and 70 allow laser light to enter and leave the housing 10. After the laser light exits through window 70 it may be dumped or otherwise disposed of. As can be seen, when the laser beam 65 encounters a cell at focus 20 a portion of it is modulated thereby and reflected and/or refracted by the cell medium in a changed path. The beam 50 relfects off the reflective coating 48 on the wall of the chamber and arrives at secondary focus 22. The tapered light guide 56, which collects light impinging thereon from a wide range of angles, collects beam 50 and conducts the collected light, with the necessary number of reflections off of its own walls, through a filter 74 onto a light detector such as a photomultiplier tube 76. The photomulplier tube is a transducer which converts a light signal into an electrical signal representative thereof. Other equivalent detectors will be apparent to those skilled in the art. The electrical signal produced by the light detector is amplified by an amplifier 78, and enters a pulse height analyzer 80 which produces a viewable or recorded output indicative of the cell passing through secondary focus 22. FIG. 3 illustrates a typical output from analyzer 80.

In one embodiment of the invention, the laser light itself is detected by photomultiplier tube 76 as modulated by the cell. Filter 74 blocks out undesired wavelengths of light. In another embodiment of the invention, the cells may be dyed such as with Acridine Orange so that they fluoresce at a particular wavelength when excited by another wavelength. In the fluoresced light embodiment, the fluoresced wavelength light passes through filter 74 which blocks the frequency of the laser light itself so that the pulse height analyzer gets a signal representative of the fluorescent cells only. Of course, with beam splitter optics, both fluoresced and modulated laser light can be detected and processed. Such systems are known and the ellipsoidal cavity of the invention can be used therewith. One such system is taught in Mullaney et al, U.S. Pat. No. 3,824,402.

In practicing the invention, light originating from points away from the primary focus 20 is strongly defocused at the secondary focus 22. This effect enhances signal-to-noise ratio, already greatly improved using the ellipsoidal cavity which utilizes much of the available light, about 75%, compared to the 3% used by prior art devices.

The tapered light guide 56 which picks up light at the secondary focus provides a great range of acceptance angles for light rays reaching the secondary focus. This also aids in greatly increasing the amount of light received by a light detector in comparison with the prior art devices. As previously indicated, the prior art flow chambers collect approximately 3% of the available fluorescent light whereas the flow chamber of the invention collects about 75% of the available light. This increase is partially due to the use of the tapered light guide in combination with the ellipsoidal flow chamber. However it will be apparent to those skilled in the art that other light guides which collect great amounts of light at the secondary focus may also be used in practicing the invention.

As can be seen, the flow chamber of the invention is highly useful for analyzing the light from very weakly fluorescing dyes. The flow chamber also provides for the use of smaller and consequently less expensive lasers for fluorescence work than do prior art devices.

The flow chamber of the invention has enabled for the first time Acridine Orange stained E. Coli bacteria intersecting a 488 nm laser beam to be measured on the basis of cellular fluorescent intensity. It is thought the invention may be used to count bacteria from a sewage plant effluent as well as the PNA distributions at various points in the life cycle of bacteria, both of which were never before measurable using optical flow cellular flow apparatus and methods.

The various features and advantages of the invention are thought to be clear from the foregoing description. However, various other features and advantages not specifically enumerated will undoubtedly occur to those versed in the art, as likewise will many variations and modifications of the preferred embodiment illustrated, all of which may be achieved without departing from the spirit and scope of the invention as defined by the following claims.

We claim:

1. A cell flow and fluorescence detector comprising;
    an essentially ellipsoidal flow chamber having primary and secondary foci and having walls at least somewhat reflective in a selected portion of the spectrum;
    means for passing cells through said primary focus;
    means for illuminating said cells at said primary focus so that the light after passing through said cells impinges on and reflects from said walls; and
    means for detecting said reflected light at said secondary focus as modulated by the cells passing through said primary focus.

2. The invention of claim 1 wherein said ellipsoidal flow chamber is gold plated to provide reflectivity in said selected portion of the spectrum.

3. The invention of claim 1 wherein said light detection means comprises a light guide tapering from a relatively large aperture for receiving light from said secondary focus to a relatively smaller aperture through which said light exits.

4. A cell flow and fluorescence detector comprising;
    an essentially ellipsoidal flow chamber having primary and secondary foci and having walls at least somewhat reflective in a selected portion of the spectrum;
    means for passing cells through said primary focus;
    means for introducing radiation onto said cells at said primary focus to cause said cells to fluoresce; and
    means for detecting said fluorescence at said secondary focus produced by the cells passing through said primary focus.

* * * * *